(12) United States Patent
Zheng et al.

(10) Patent No.: US 10,720,255 B2
(45) Date of Patent: Jul. 21, 2020

(54) RADIATION DELIVERY DEVICES AND APPLICATIONS THEREOF

(71) Applicant: Clemson University Research Foundation, Clemson, SC (US)

(72) Inventors: Xiao Ran Zheng, Clemson, SC (US); Endre Takacs, Seneca, SC (US); Mark Leising, Seneca, SC (US)

(73) Assignee: Clemson University, Clemson, SC (US)

( * ) Notice: Subject to any disclaimer, the term of this patent is extended or adjusted under 35 U.S.C. 154(b) by 0 days.

(21) Appl. No.: 15/643,076

(22) Filed: Jul. 6, 2017

(65) Prior Publication Data

US 2018/0012675 A1 Jan. 11, 2018

Related U.S. Application Data

(60) Provisional application No. 62/359,051, filed on Jul. 6, 2016.

(51) Int. Cl.
| | |
|---|---|
| *G21K 1/02* | (2006.01) |
| *A61N 5/10* | (2006.01) |
| *G21K 5/04* | (2006.01) |

(52) U.S. Cl.
CPC ........... *G21K 1/025* (2013.01); *A61N 5/1042* (2013.01); *A61N 5/1084* (2013.01); *G21K 5/04* (2013.01); *A61N 2005/1094* (2013.01); *G21K 1/02* (2013.01)

(58) Field of Classification Search
CPC ............... A61N 5/1042; A61N 5/1084; A61N 2005/0194; G21K 1/025; G21K 1/02; G21K 10/02; G21K 5/04
See application file for complete search history.

(56) References Cited

U.S. PATENT DOCUMENTS

| | | | |
|---|---|---|---|
| 4,780,898 A | 10/1988 | Sundqvist | |
| 5,757,886 A | 5/1998 | Song | |
| 6,044,126 A * | 3/2000 | Rousseau | A61N 5/1031 378/148 |
| 6,201,988 B1 * | 3/2001 | Bourland | A61N 5/1031 378/65 |

(Continued)

FOREIGN PATENT DOCUMENTS

| | | |
|---|---|---|
| CN | 1736510 A | 2/2006 |
| CN | 104001269 A | 6/2014 |

(Continued)

OTHER PUBLICATIONS https://en.wikipedia.org/wiki/Radiosurgery, retrieved Dec. 25, 2014.*

*Primary Examiner* — Wyatt A Stoffa
(74) *Attorney, Agent, or Firm* — J. Clinton Wimbish; Nexsen Pruet, PLLC

(57) ABSTRACT

Radiation delivery devices are described herein having compact and lightweight design in comparison to existing architectures. A radiation delivery device comprises a source body including a plurality of radiation sources and a collimator component for directing radiation from the radiation sources to a common focal area, wherein the radiation sources are arranged within the collimator component. In some embodiments, for example, the source body is positioned within an interior cavity of the collimator component.

25 Claims, 17 Drawing Sheets

(56) References Cited

U.S. PATENT DOCUMENTS

| | | | |
|---|---|---|---|
| 6,389,108 B1 * | 5/2002 | Ein-Gal | G21K 1/04 250/505.1 |
| 6,438,203 B1 | 8/2002 | Shipeng et al. | |
| 6,512,813 B1 * | 1/2003 | Krispel | A61N 5/1042 378/64 |
| 6,865,254 B2 | 3/2005 | Nafstadius | |
| 6,914,959 B2 | 7/2005 | Bailey et al. | |
| 6,931,096 B2 | 8/2005 | Carlsson et al. | |
| 6,968,036 B2 * | 11/2005 | Carlsson | A61N 5/1084 378/65 |
| 7,603,164 B2 | 10/2009 | Uematsu | |
| 7,659,530 B2 * | 2/2010 | Qiu | A61N 5/1084 250/492.1 |
| 7,826,593 B2 | 11/2010 | Svensson et al. | |
| 8,788,017 B2 * | 7/2014 | Yu | A61N 5/1084 600/411 |
| 9,687,200 B2 | 6/2017 | Maurer, Jr. | |
| 2004/0018577 A1 | 1/2004 | Emerson Campbell et al. | |
| 2004/0136495 A1 * | 7/2004 | Carlsson | A61N 5/1084 378/65 |
| 2004/0184577 A1 * | 9/2004 | Carlsson | A61N 5/1084 378/65 |
| 2008/0029719 A1 * | 2/2008 | Qiu | A61N 5/1084 250/515.1 |
| 2008/0253516 A1 | 10/2008 | Hui et al. | |
| 2010/0054408 A1 | 3/2010 | Echner | |
| 2010/0094119 A1 * | 4/2010 | Yu | A61N 5/1084 600/411 |
| 2017/0007850 A1 | 1/2017 | Carlsson | |
| 2019/0001146 A1 * | 1/2019 | Liu | A61N 5/01 |

FOREIGN PATENT DOCUMENTS

| | | |
|---|---|---|
| EP | 0582508 A1 | 2/1994 |
| EP | 1419801 A1 | 5/2004 |
| EP | 2539020 B1 | 1/2013 |
| RU | 2343459 C1 | 1/2009 |
| WO | 2016011604 A1 | 1/2016 |

* cited by examiner

RADIATION DELIVERY DEVICES AND APPLICATIONS THEREOF

RELATED APPLICATION DATA

The present application claims priority pursuant to 35 U.S.C. § 119(e) to U.S. Provisional Patent Application 62/359,051, filed Jul. 6, 2016, which is incorporated herein by reference in its entirety.

FIELD

The present invention relates to apparatus for delivering radiation from multiple sources to a common focal point and, in particular, to radiation delivery devices for therapies including stereotactic radiosurgery (SRS) and stereotactic body radiotherapy (SBRT).

BACKGROUND

A number of radiation therapies have been developed over the years for treating various diseased tissues, such as cancerous tissues. Significant efforts have been devoted to improving radiation therapies by increasing the accuracy and precision of delivered radiation, thereby limiting damage to neighboring healthy tissue. SRS and SBRT, for example, are advanced therapies employing many precisely focused radiation beams to treat tumors and various abnormalities in the brain, neck and other regions of the body. Each radiation beam has very little effect on the tissue the beam passes through. However, when the beams are collectively focused at a common point or area, the radiation dosage is sufficient to destroy or damage the diseased tissue.

Several SRS machines of differing construction and radiation source are currently available. Photon beam or linear accelerator (LINAC) machines use a single X-ray source for treating diseased brain and/or body tissue. Proton beam or heavy charged particle radiosurgery is another single source device. Access to proton beam radiosurgery is generally limited due to extreme costs associated with building and installation of proton beam apparatus. Alternatively, multi-source devices are also available. Gamma Knife® apparatus, for example, employs multiple (e.g. up to 201) individual gamma ray sources compartmentalized at uniform radial positions in a conical or hemispherical source body. A collimator body is positioned within the source body to direct the gamma ray beams to a common focal point in the patient's brain or body. Moreover, the source body is arranged in a shielding body to preclude radiation exposure to the external environment. Shielding apparatus is generally very large and bulky, often weighing up to 20 tons. Such weight complicates installation of Gamma Knife® apparatus and can require updates to facility infrastructure to ensure proper load support. Additionally, shielding apparatus requires the patient be moved into a closed cylindrical treatment chamber, which can cause discomfort for patients suffering from claustrophobia.

SUMMARY

In view of the foregoing disadvantages, radiation delivery devices having new architectures are provided. In some embodiments, radiation delivery devices described herein have compact and lightweight design in comparison to existing architectures. A compact and lightweight design can facilitate installation of the device and simplify use of the device to treat diseased tissues at various body locations.

Briefly, a radiation delivery device comprises a source body including a plurality of radiation sources and a collimator component for directing radiation from the radiation sources to a common focal area, wherein the radiation sources are arranged within the collimator component. In some embodiments, for example, the source body is positioned within an interior cavity of the collimator component. Having the radiation sources arranged within the collimator component marks a fundamental departure from prior radiation delivery devices where the source body surrounds the collimators. Radiation delivery devices described herein can be configured for integration with SRS and/or SBRT apparatus.

In another aspect, methods of directing radiation are provided. In some embodiments, a method of directing radiation from a plurality of radiation sources comprises positioning a source body comprising the radiation sources within an interior cavity of a collimator component and directing the radiation to the common focal area with the collimator component. As described further herein, the collimator component can comprise a primary collimator body including one or more sets of primary collimator passages for directing the radiation. The source body and/or primary collimator body can be rotated to align the radiation sources with the primary collimator passages. The collimator component may also comprise at least one additional collimator body having one or more sets of additional collimator passages for directing the radiation to the common focal point. In some embodiments, the additional collimator body is rotated to align a set of additional collimator passages with the primary collimator passages.

These and other embodiments are further described in the following detailed description.

DETAILED DESCRIPTION

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In one aspect, radiation delivery devices are provided. A radiation delivery device comprises a source body including a plurality of radiation sources and a collimator component for directing radiation from the radiation sources to a common focal area, wherein the radiation sources are arranged within the collimator component. In some embodiments, for example, the source component and associated radiation sources are positioned within an interior cavity of the collimator component. The source body can have any design and any number of individual radiation sources permitted by the surrounding collimator component. In some embodiments, for example, the source body comprises a surface extending along the longitudinal axis of the body. Individual radiation sources can be arranged in apertures or capsules along the surface. In some embodiments, the radiation sources are arranged in a line or linear array along the longitudinal surface. In some embodiments, the longitudinal surface comprising the apertures or capsules exhibits curvature. The surface can have any curvature consistent with delivery of radiation to a common focal area in conjunction with the collimator component. For example, the longitudinal curved surface can exhibit an arcuate shape, such as a hyperbolic arc. Alternatively, surface does not exhibit curvature in the longitudinal direction. Moreover, the common focal area of radiation delivery devices described herein can have any diameter and/or shape not inconsistent with the objectives of the present invention. In some embodiments, the common focal area has a diameter of 2 mm to 60 mm. The common focal area can also exhibit a circular, elliptical or polygonal shape.

Figure 1:
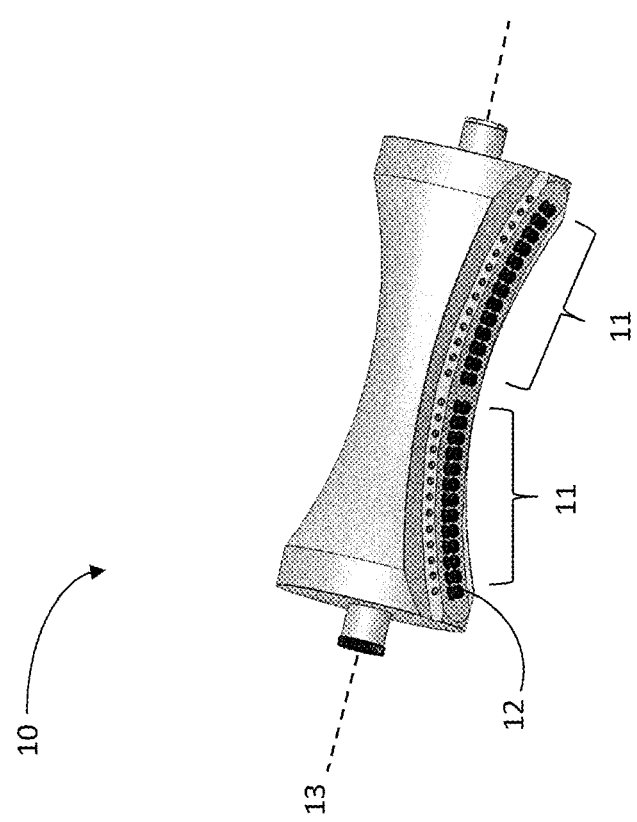
FIG. 1 illustrates a source body according to some embodiments described herein.
Figure 2:
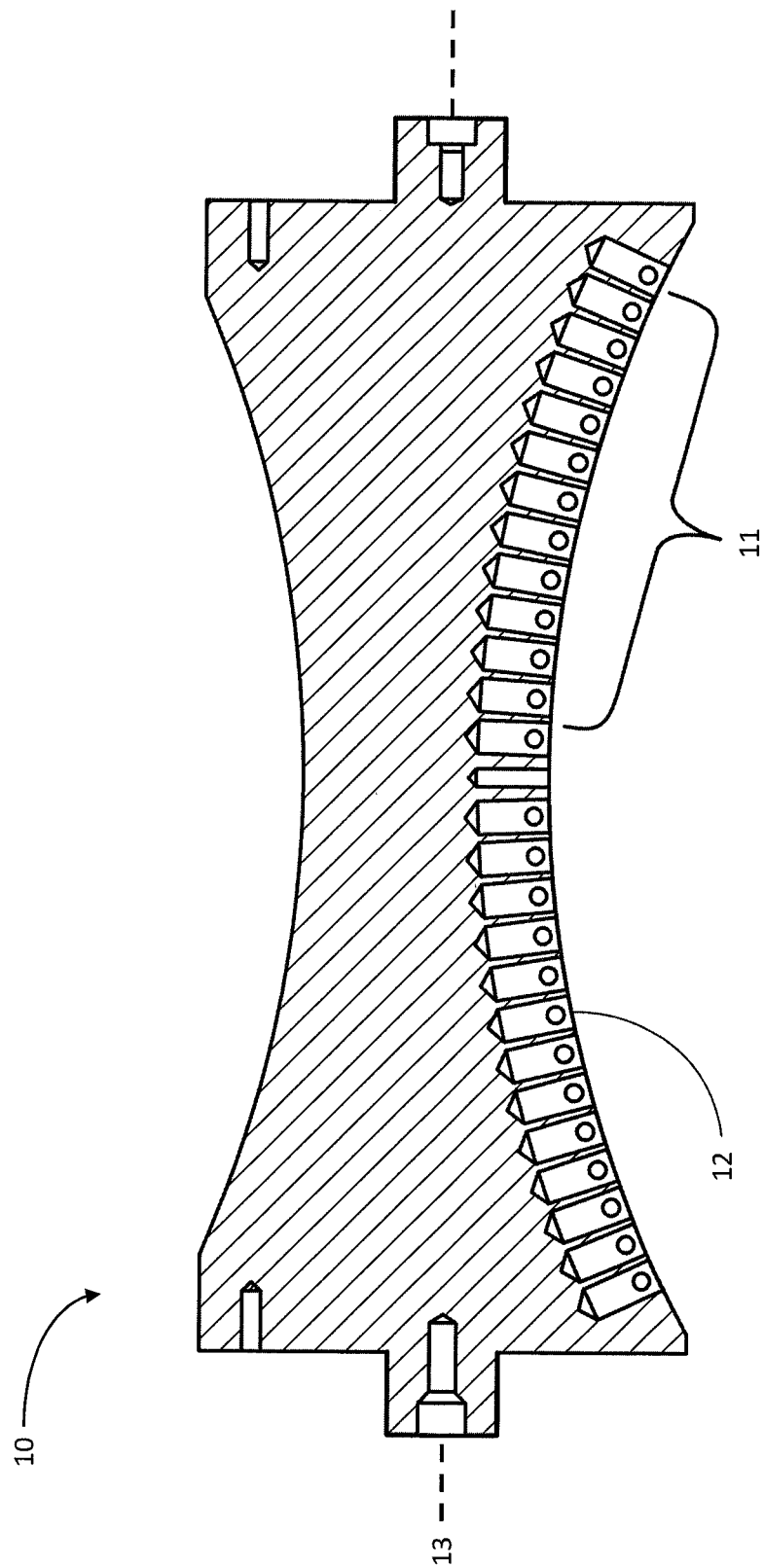
FIG. 2 illustrates a cross-sectional view of a source body according to some embodiments described herein.

FIG. 1 illustrates a perspective view of a source body according to some embodiments described herein. The source body 10 generally follows the shape of a hyperbolic cylinder. A plurality of individual radiation sources 11 are arranged in apertures 12 along the longitudinal axis 13 of the source body 10. In the embodiment of FIG. 1, the source body 10 further comprises cylindrical protrusions for engaging drive apparatus for rotating the source body 10 between on and off positions as described further herein. FIG. 2 illustrates a cross-sectional view of the source body 10 in FIG. 1. As provided in FIG. 2, apertures 12 are arranged in the hyperbolic cylindrical surface and extend in a line along the longitudinal axis 13 of the source body 10. Radiation sources 11 are positioned in the apertures 12. The remainder of the source body 10 can be of a solid construction to assist in shield radioactive radiations sources.

Figure 11:
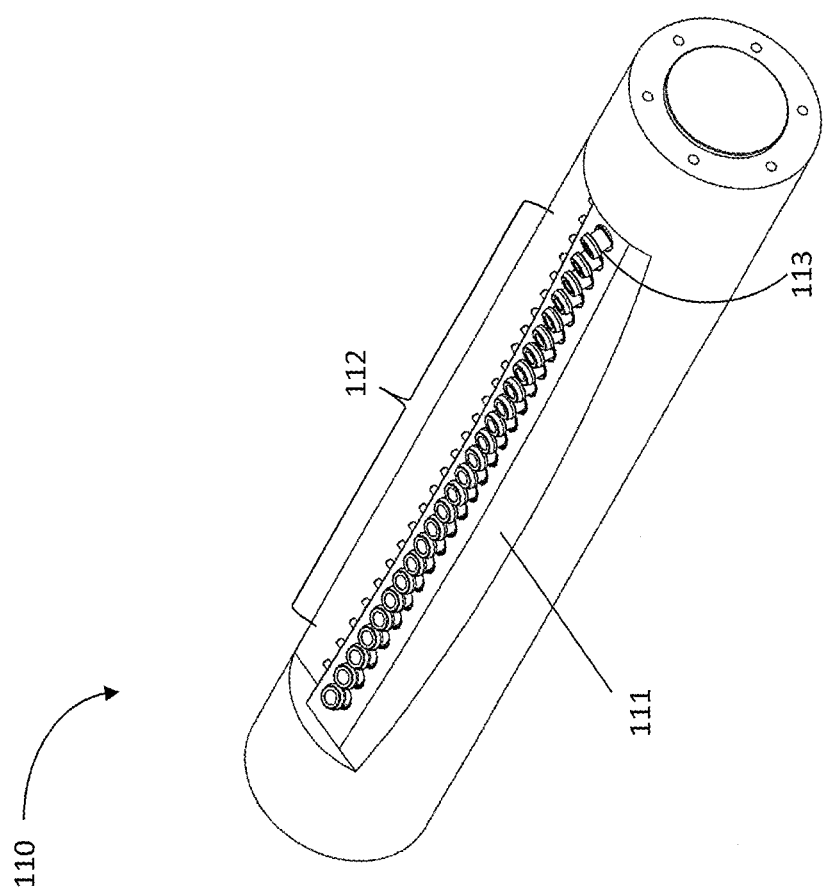
FIG. 11 illustrates a perspective view of a source body according some embodiments described herein.
Figure 12:
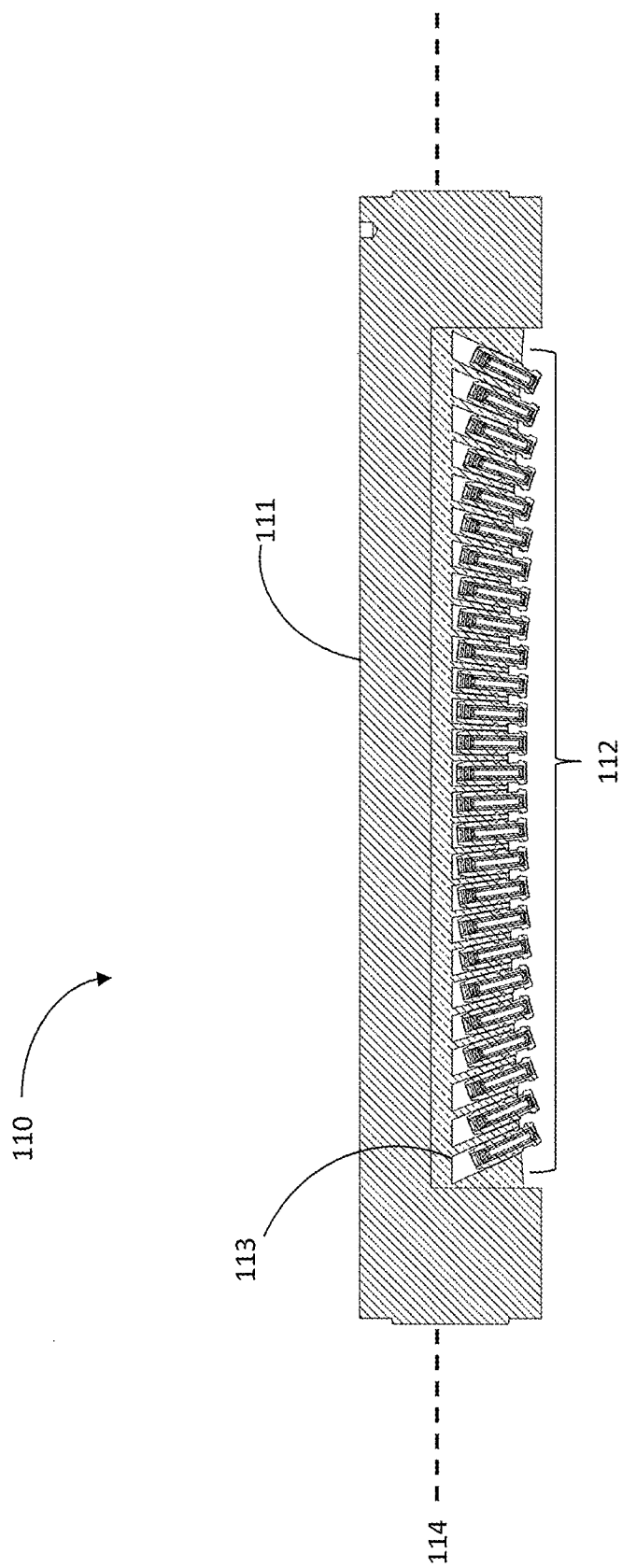
FIG. 12 illustrates a cross-sectional view of a source body according to some embodiments described herein.

FIG. 11 illustrates a perspective view of a source body according additional embodiments described herein. The source body 110 is in the shape of a cylinder. In contrast to FIG. 1, the cylinder does not exhibit a hyperbolic shape. Accordingly, the longitudinal surface 111 comprising individual radiation sources 112 arranged in apertures 113 is flat or otherwise does not exhibit curvature in the longitudinal direction. The remainder of the source body 110 can be of a solid construction to assist in shielding the radioactive radiation sources. FIG. 12 illustrates a cross-sectional view of the source body 110 in FIG. 11. As provided in FIG. 12, apertures 113 are arranged in the cylindrical surface and extend in a line along the longitudinal axis 114 of the source body 110. Radiation sources 112 are positioned in the apertures 113. Notably, the apertures 113 are angled for delivery of radiation to a common focal area in conjunction with the collimator component. Angled apertures 113 can permit use of a cylindrical source body that is not curved in a direction extending along the longitudinal axis 114. Such embodiments can simplify source body construction by obviating hyperbolic cylinders and/or other complex shapes. Moreover, specific angle of an individual aperture 113 can be dependent on the position of the aperture 113 along the cylinder. As illustrated in FIG. 12, apertures 113 located proximate the cylinder ends can exhibit greater angles relative to apertures 113 positioned at the center of the cylinder.

The source body can employ any radiation sources not inconsistent with the objectives of the present invention. In some embodiments, the individual radiation sources are radioactive material exhibiting gamma emission. For example, one or more of cobalt-60, iridium-192 and cesium 137 can find application as individual radiation sources. In other embodiments, radiation sources can have emission in other regions of the electromagnetic spectrum, such as in the X-ray region.

Contrary to prior designs, the source component and associated radiation sources are positioned within the collimator component. The collimator component comprises a primary collimator body. In some embodiments, the primary collimator body comprises an interior cavity or compartment for housing the source body. A set of primary collimator passages for directing radiation from the radiation sources is positioned along the wall of the primary collimator body. In some embodiments, the primary collimator body comprises multiple sets of primary collimator passages. The sets of primary collimator passages can differ from one another in diameter and/or shape permitting variation in size and/or shape of the focal area. Sets of differing primary collimator passages can be radially spaced around the wall of the primary collimator body. Further, the primary collimator body can have any shape not inconsistent with the objectives of the present invention. In some embodiments, the primary collimator body comprises a curved surface extending along the longitudinal axis of the body. For example, the curved surface can exhibit an arcuate shape matching or substantially matching the arcuate shape of the source body. In one embodiment, the primary collimator body and source body are both hyperbolic cylinders. The primary collimator body may also comprise gearing or other apparatus for engaging a drive. The drive can rotate the collimator body relative to the source body and/or additional collimator bodies.

Figure 3:
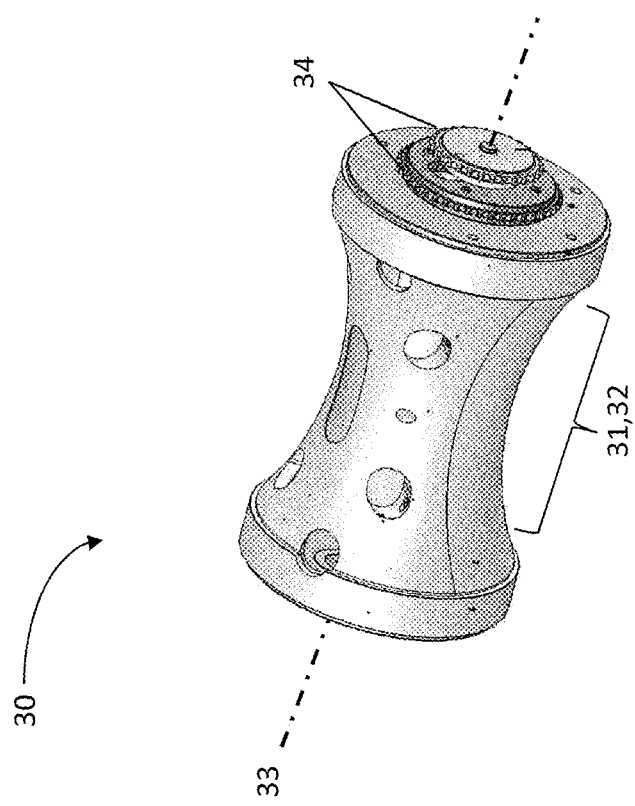
FIG. 3 illustrates a perspective view of a primary collimator body according to some embodiments described herein.
Figure 4:
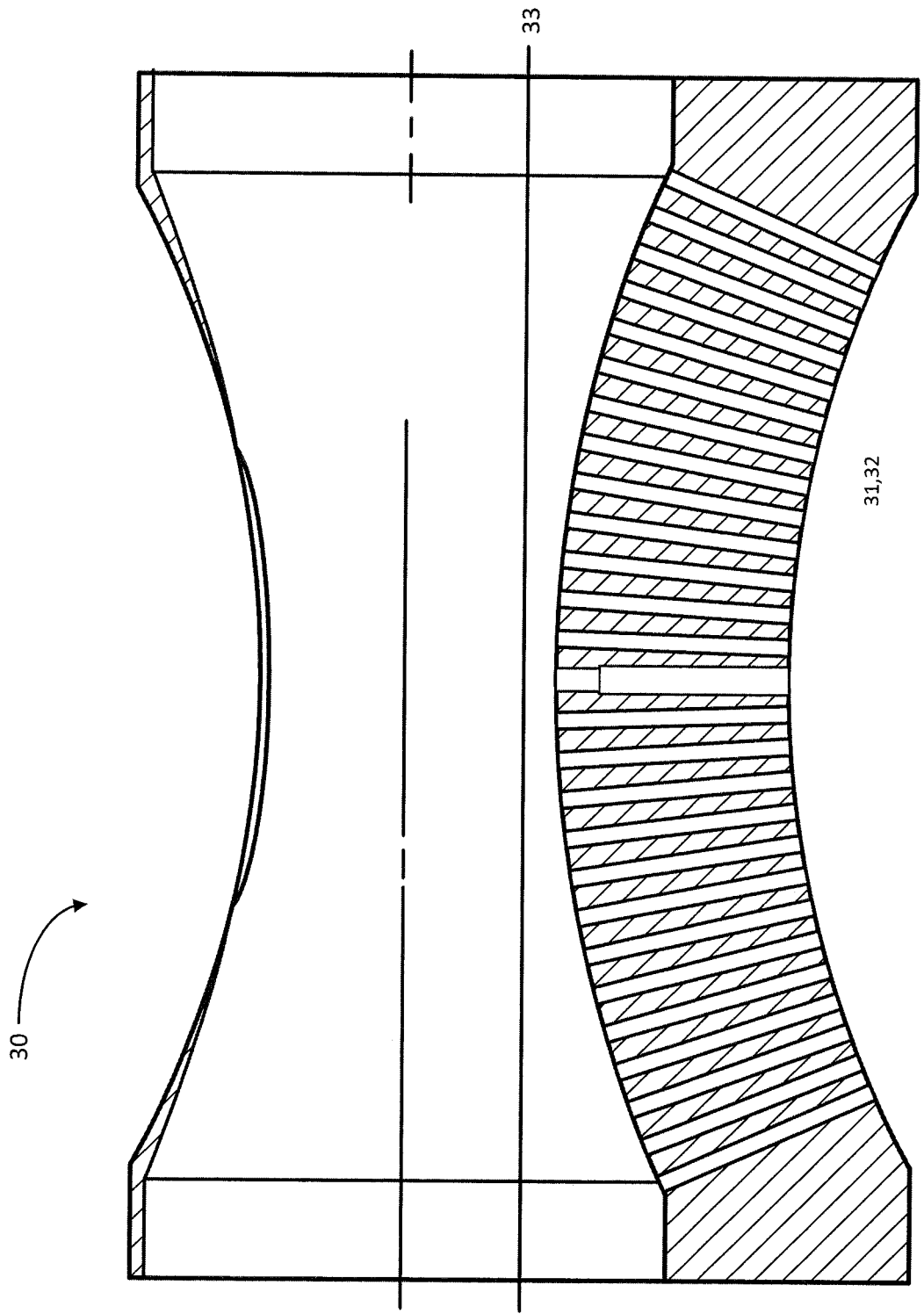
FIG. 4 illustrates a cross-sectional view of a primary collimator body according to some embodiments described herein.

FIG. 3 illustrates a perspective view of a primary collimator body according to some embodiments described herein. The primary collimator body 30 is a hollow hyperbolic cylinder for receiving the source body therein. A set of primary collimator passages 31 is positioned along the curved surface 32 extending along the longitudinal axis 33 of the primary collimator body 30. The primary collimator body of FIG. 3 also comprises gears 34 for engaging rotational drive apparatus. FIG. 4 illustrates a cross-sectional view of the primary collimator body of FIG. 3. As provided in FIG. 4, the primary collimator passages 31 extend through the curved wall 32 of the body 30. Moreover, curvature of the primary collimator body 30 matches or substantially matches curvature of the source body 10 of FIG. 2 permitting proper alignment of the radiation sources 11 and collimator passages 31.

Figure 13:
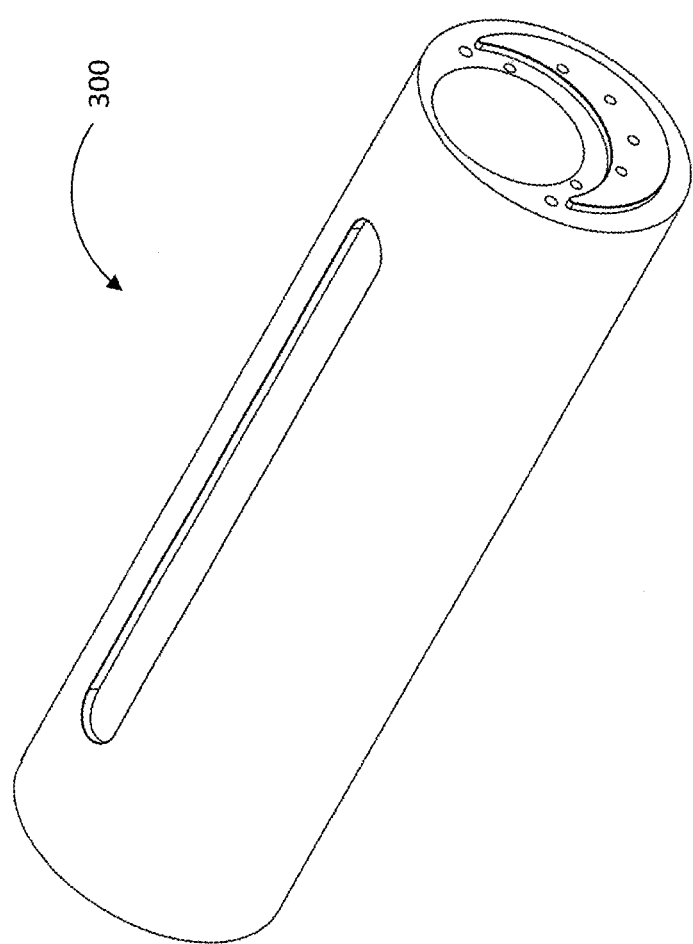
FIG. 13 illustrates a perspective view of a primary collimator body according to some embodiments described herein.
Figure 14:
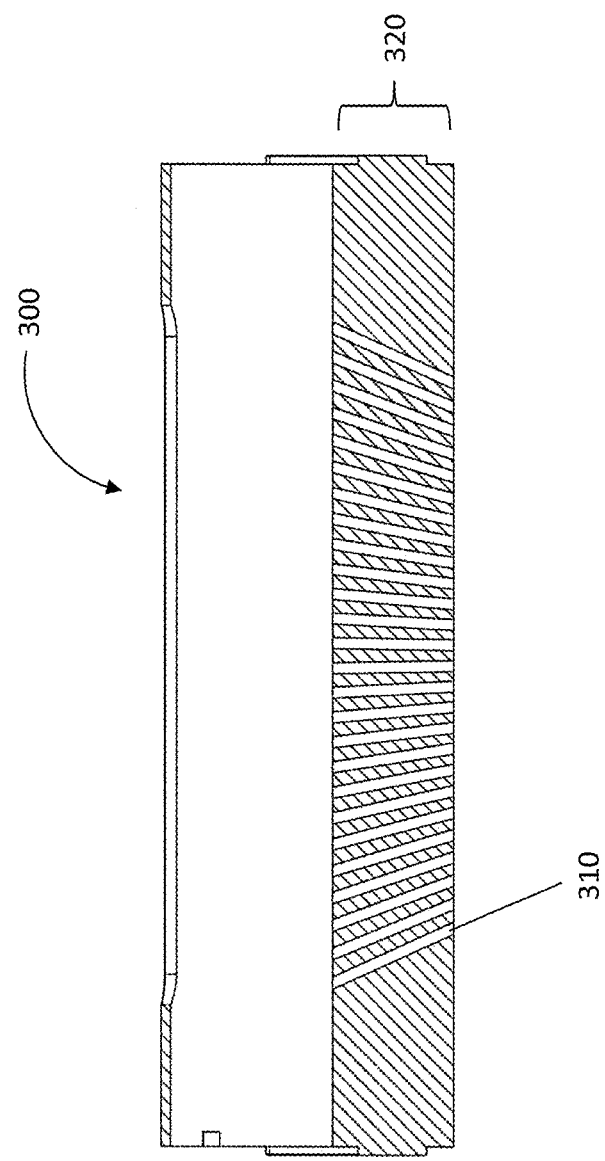
FIG. 14 illustrates a cross-sectional view of a primary collimator body according to some embodiments described herein.

FIG. 13 illustrates a perspective view of a primary collimator body according to additional embodiments described herein. The primary collimator body 300 is a hollow cylinder for receiving the source body therein. In the embodiment of FIG. 13, the cylindrical primary collimator does not exhibit a hyperbolic shape or other curved shape along the longitudinal axis. Ends of the primary collimator body 300 are configured for coupling to or engaging rotational drive apparatus. FIG. 14 illustrates a cross-sectional view of the primary collimator body of FIG. 13. The primary collimator body 300 comprises collimator passages 310 extending through the cylinder wall 320. Angles of the collimator passages can match or substantially match angles of the apertures 113 of FIG. 12, thereby permitting proper alignment of the radiation sources 112 and collimator passages 310.

The radiation delivery device, in some embodiments, further comprises at least one additional collimator body including one or more sets of additional collimator passages for directing radiation from the radiation sources to the common focal area. In some embodiments, the additional collimator body comprises multiple sets of additional collimator passages. The multiple sets may be radially spaced around the wall of the additional collimator body. Sets of additional collimator passages may differ from one another in size and/or shape, thereby permitting variation of focal area size and/or shape according to the specific set selected for directing the radiation. In some embodiments, an additional collimator body may have 2-15 sets of additional collimator passages.

Sets of additional collimator passages may also differ from primary collimator passages in size and/or shape. Further, the number of additional collimator passages in a set may be equal or unequal to the number of primary collimator passages. In some embodiments, the number of additional collimator passages is less than the number of primary collimator passages. Fewer additional collimator passages can preclude radiation from all the radiation sources from reaching the focal area. In such embodiments, the radiation dose level can be varied. Moreover radiation entry points into the patient can be altered to avoid irradiation of sensitive organs or tissue.

An additional collimator body can have any shape not inconsistent with the objectives of the present invention. The additional collimator body, for example, can comprise an interior cavity for receiving an adjacent collimator body such as the primary collimator body and associated source body. In some embodiments, the additional collimator body comprises a curved surface extending along the longitudinal axis of the body. For example, the curved surface can exhibit an arcuate shape matching or substantially matching the arcuate shape of an adjacent collimator body, such as the primary collimator body. In one embodiment, the additional collimator body and primary body are both hyperbolic cylinders. The additional collimator body may also comprise gearing or other apparatus for engaging a drive. The drive can rotate the collimator body relative to an adjacent collimator body and/or source body for directing the radiation to the focal area.

Figure 5:
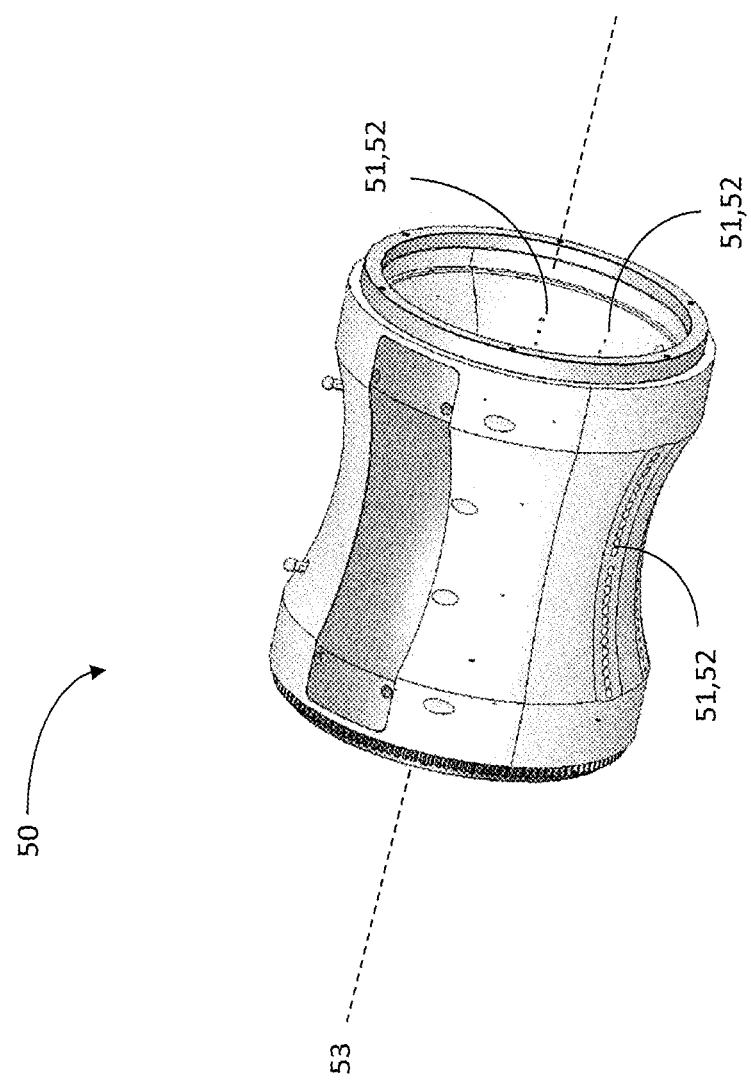
FIG. 5 illustrates an additional collimator body according to some embodiments described herein.
Figure 6:
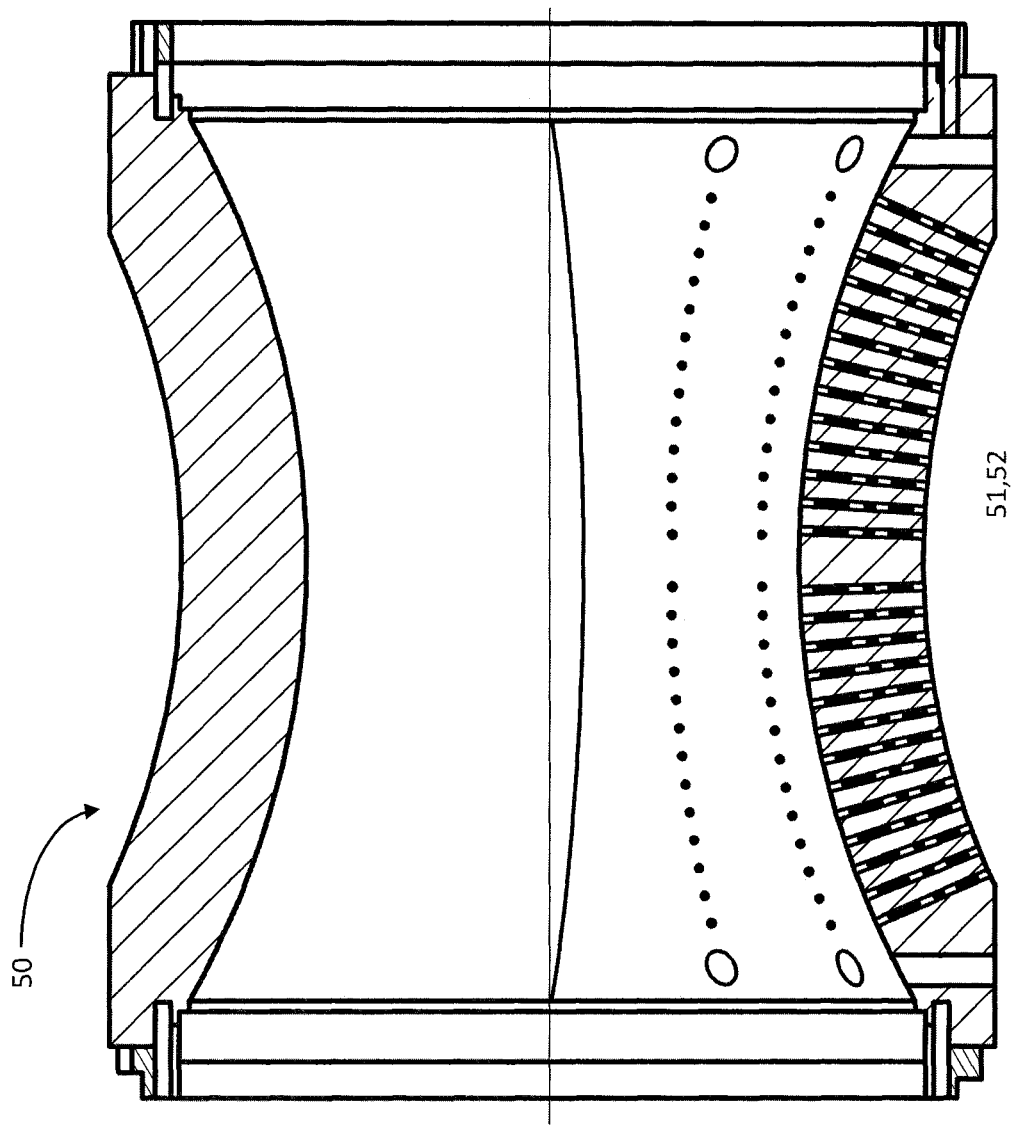
FIG. 6 illustrates a cross-sectional view of an additional collimator body according to some embodiments described herein.

FIG. 5 illustrates an additional collimator body according to some embodiments described herein. The additional collimator body 50 is a hollow hyperbolic cylinder for receiving the primary collimator body and associated source body contained in the primary collimator body. By receiving the primary collimator body, the additional collimator body can be considered a secondary collimator body. As described herein, any number of additional collimator bodies is contemplated including tertiary, quaternary, quinary collimator bodies and so on. The additional collimator body 50 comprises sets 51 of additional collimator passages 52. The sets 51 are radially spaced around the collimator body 50, with each set 51 extending in a line along the longitudinal axis 53 of the body 50. Each set 51 of additional collimator passages 52 can offer a different focal area size and/or shape permitting tailoring of the radiation dose. The additional collimator body may further comprise apparatus for engaging a drive. The drive may rotate the additional collimator body to permit selection of the desired set 51 of additional collimator passages 52. FIG. 6 illustrates a cross-sectional view of the additional collimator body of FIG. 5. As provided in FIG. 6, a set 51 of additional collimator passages 52 is arranged along the arcuate surface of the collimator body 50.

Figure 7:
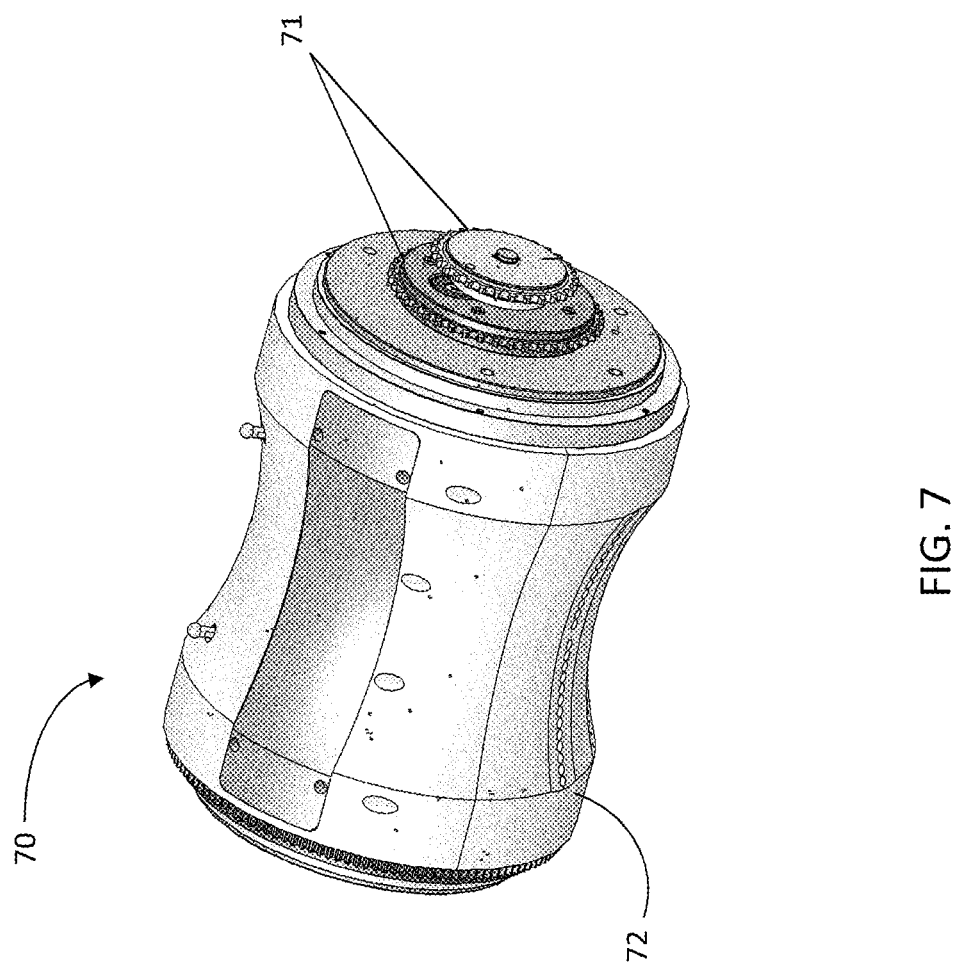
FIG. 7 illustrates assembly of a source body, primary collimator body and secondary collimator body according to some embodiments.

FIG. 7 illustrates assembly of the source body, primary collimator body and additional (secondary) collimator body according to some embodiments. Drive gearing 71 is provided at one end of the assembly 70 for rotation of the source body and primary collimator body contained within the secondary collimator body 72.

Figure 15:
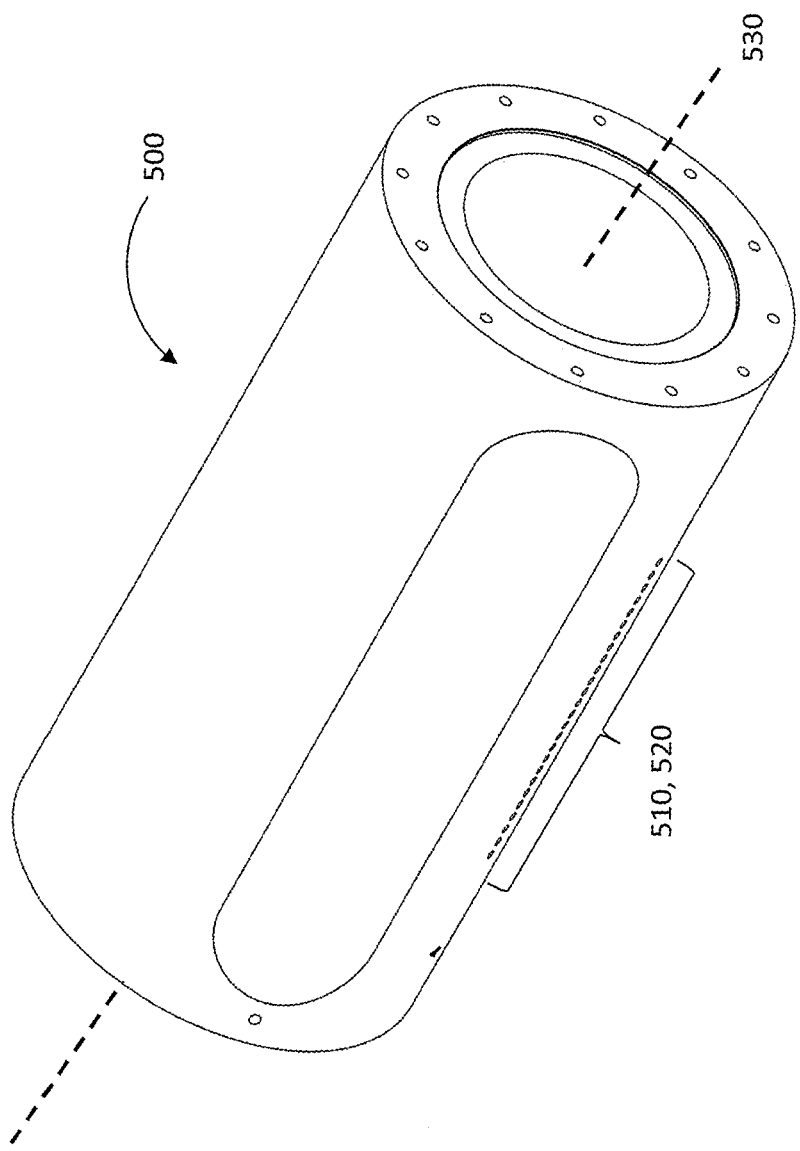
FIG. 15 illustrates an additional collimator body according to some embodiments described herein.
Figure 16:
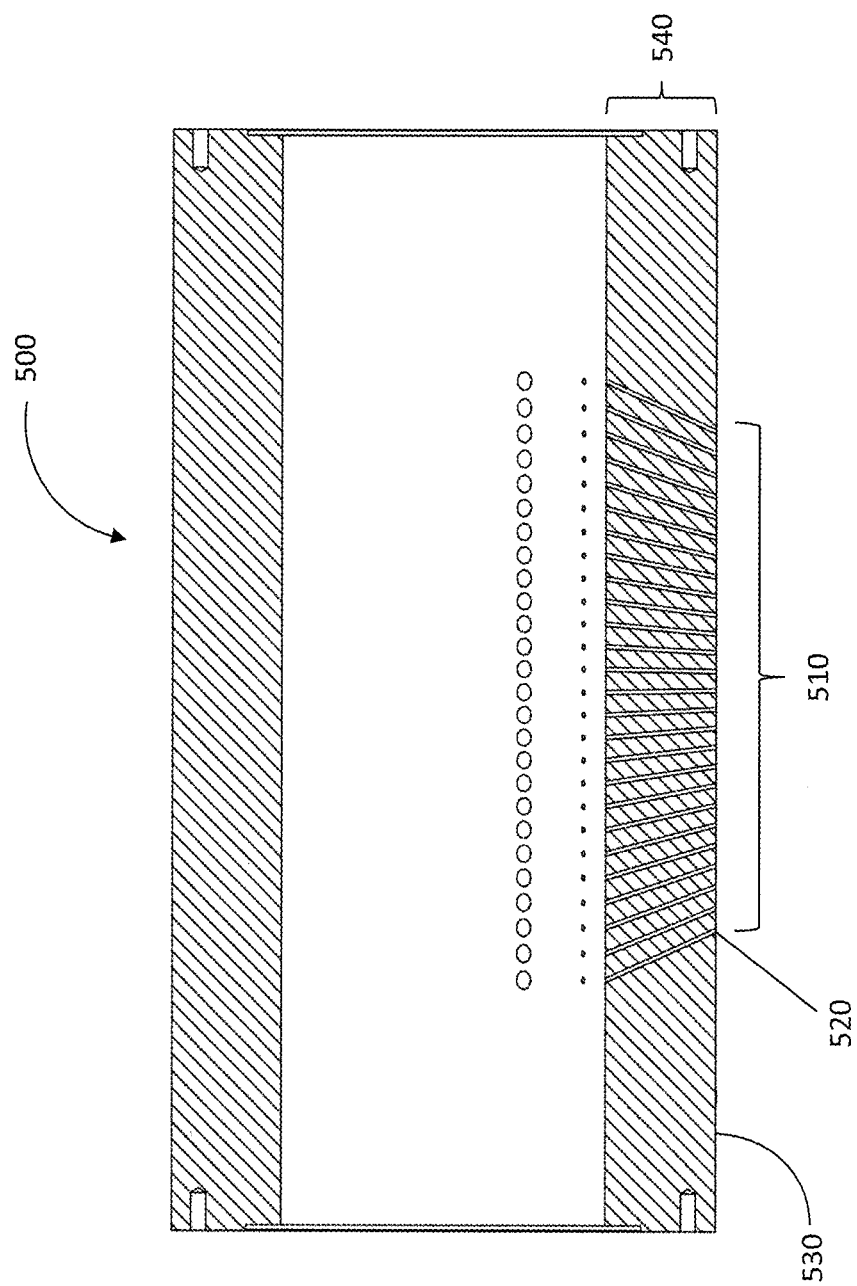
FIG. 16 illustrates a cross-sectional view of an additional collimator body according to some embodiments described herein.

FIG. 15 illustrates an additional collimator body according to other embodiments described herein. The additional collimator body 500 is a hollow cylinder for receiving the primary collimator body and associated source body contained in the primary collimator body. In the embodiment of FIG. 15, the cylinder does not exhibit a hyperbolic shape or other curved shape along the longitudinal axis. By receiving the primary collimator body, the additional collimator body 500 can be considered a secondary collimator body. Alternatively, the additional collimator body 500 can be tertiary, quaternary, quinary and so on. The additional collimator body 500 comprises sets 510 of additional collimator passages 520. The sets 510 are radially spaced around the collimator body 500, with each set 510 extending in a line along the longitudinal axis 530 of the body 500. Each set 510 of additional collimator passages 520 can offer a different focal area size and/or shape permitting tailoring of the radiation dose. The additional collimator body may further comprise apparatus for engaging a drive. The drive may rotate the additional collimator body to permit selection of the desired set 510 of additional collimator passages 520. FIG. 16 illustrates a cross-sectional view of the additional collimator body of FIG. 15. As provided in FIG. 16, a set 510 of additional collimator passages 520 is arranged along the flat or non-curved surface 530 of the collimator body 500 and extend through the wall 540 of the body 500.

As described herein, the source body, primary collimator body and/or additional collimator body can be rotated.

Rotation of these components can be in concert or independent of one another. For example, the source body can be rotated into an "off" position wherein the radiation sources face a shielding body of the radiation delivery apparatus. When desired, the source body can be rotated into position where the radiation sources face collimator passages of the primary collimator body and any additional collimator body. Moreover, the primary collimator body can also be rotated to serve as a beam shutter. The primary collimator body, for example, can be rotated to preclude alignment of the primary collimator passages and radiation sources, thereby shuttering the radiation sources. An additional collimator body may also be rotated in a similar manner to shutter the radiation sources. An additional collimator body is also rotated for selection of the desired set of collimator passages as described above.

Figure 8A:
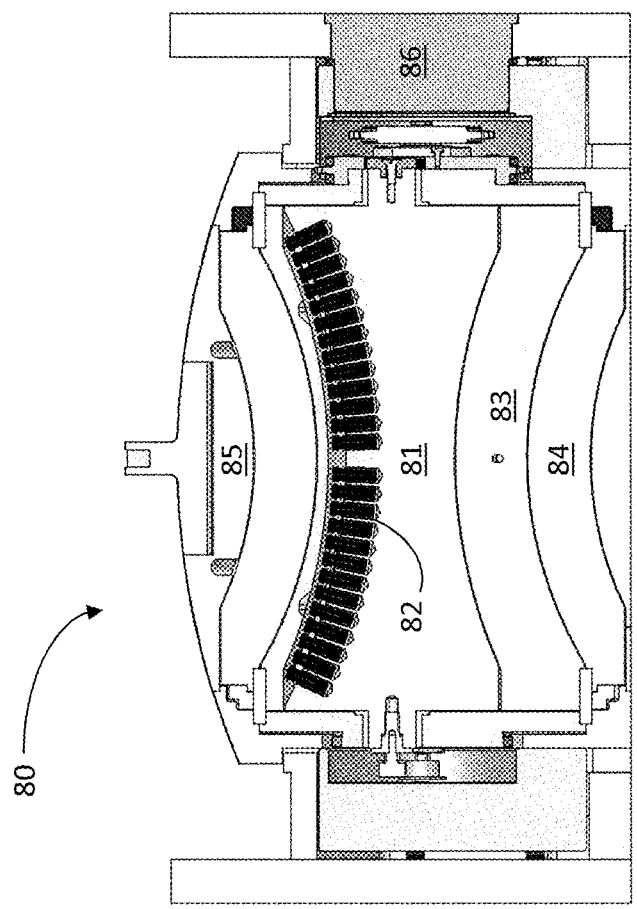
FIG. 8A illustrates a cross-sectional view of a radiation delivery device wherein the source body is rotated to the off position.
Figure 8B:
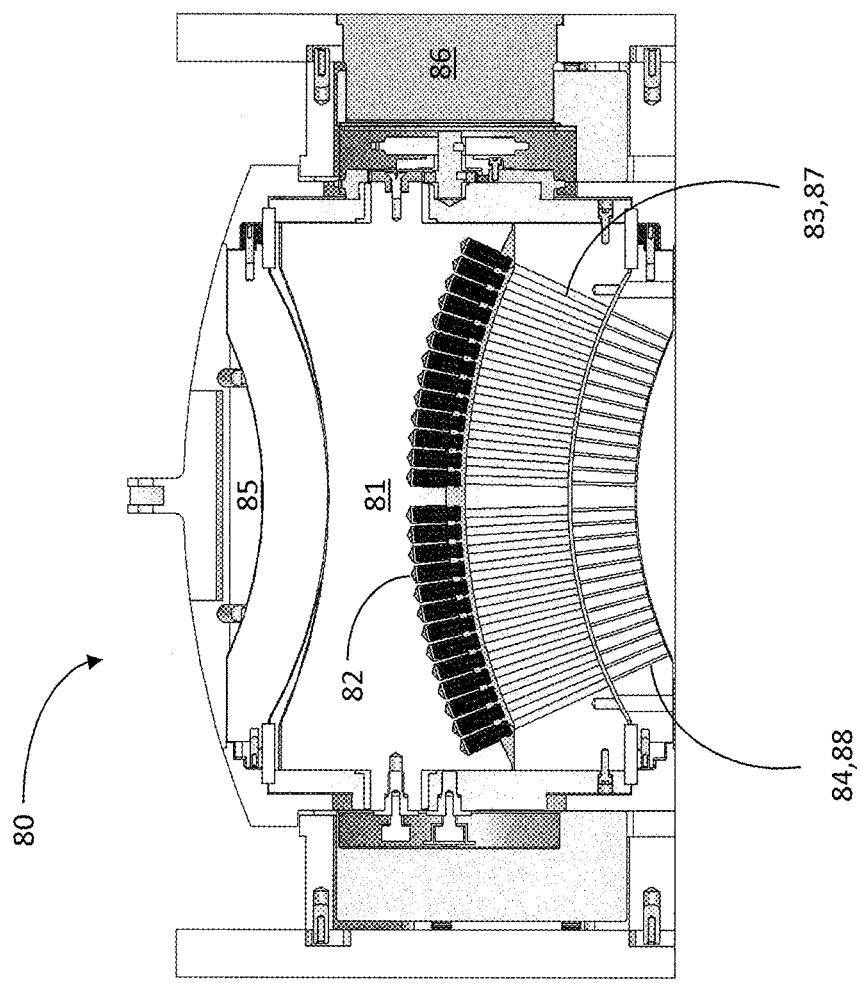
FIG. 8B illustrates a cross-sectional view of a radiation delivery device wherein the source body is rotated to the on position.

FIG. 8A illustrates a cross-sectional view of a radiation delivery device wherein the source body is rotated to the off position. The radiation delivery device 80 comprises a source body 81 with individual radiation sources 82. The radiation delivery device 80 also comprises a primary collimator body 83, a secondary collimator body 84, a shielding body 85 and drive apparatus 86. As illustrated in FIG. 8A, the source body and individual radiation sources 82 face the shielding body 85. The drive apparatus 86 can rotate the source body 81 into the "on" position as illustrated in FIG. 8B. In the "on" position, the radiation sources 82 are aligned with the primary collimator passages 87 and secondary collimator passages 88 for providing radiation to a common focal area.

Figure 9B:
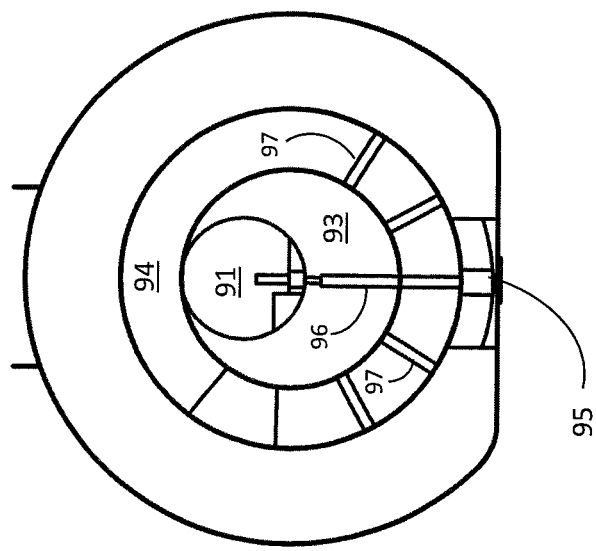
FIGS. 9A and 9B illustrate non-concentric arrangement of the source body according to some embodiments.
Figure 9A:
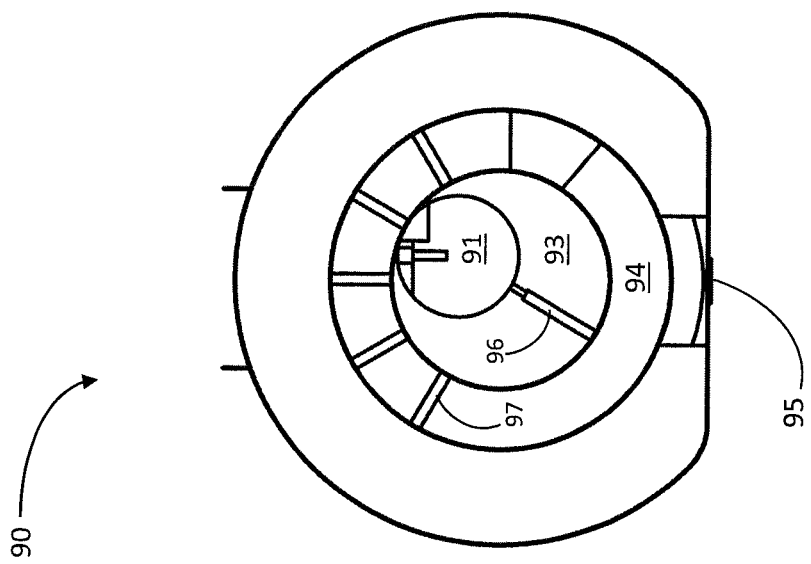

The source body, primary collimator body and/or additional collimator body, in some embodiments, have a non-concentric or eccentric arrangement. The source body, for example, can have an off-centric arrangement relative to the primary collimator body and/or additional collimator body. This off-centric arrangement can position the source body closer to the shielding body and further away from the emitting face of the radiation delivery device. Such positioning can provide enhanced shielding of the radiation sources when the device is not in operation. FIGS. 9A and 9B illustrate non-concentric arrangement of the source body according to some embodiments. In the axial cross-sectional views of FIGS. 9A and 9B, the source body 91 exhibits a non-concentric arrangement relative to the primary collimator body 93 and secondary collimator body 94. This non-concentric arrangement places the source body 91 at a further distance from the emitting face 95 of the radiation delivery device 90. When the source body 91 is rotated to the off position, as in FIG. 9A, this increased distance provides additional shielding of the radiation sources. The source body 91 can be subsequently rotated to the on position, as in FIG. 9B, where radiation passes through the primary 96 and secondary 97 collimator passages to the emitting face 95. Multiple sets 97 of secondary collimator passages are also illustrated in FIGS. 9A and 9B. Importantly, the source body, primary collimator body and/or additional collimator body can be made of one or more materials exhibiting desirable radiation shielding properties. In some embodiments, for example, these component parts of the radiation delivery device are made of tungsten or tungsten composite.

Figures 10A, 10B:
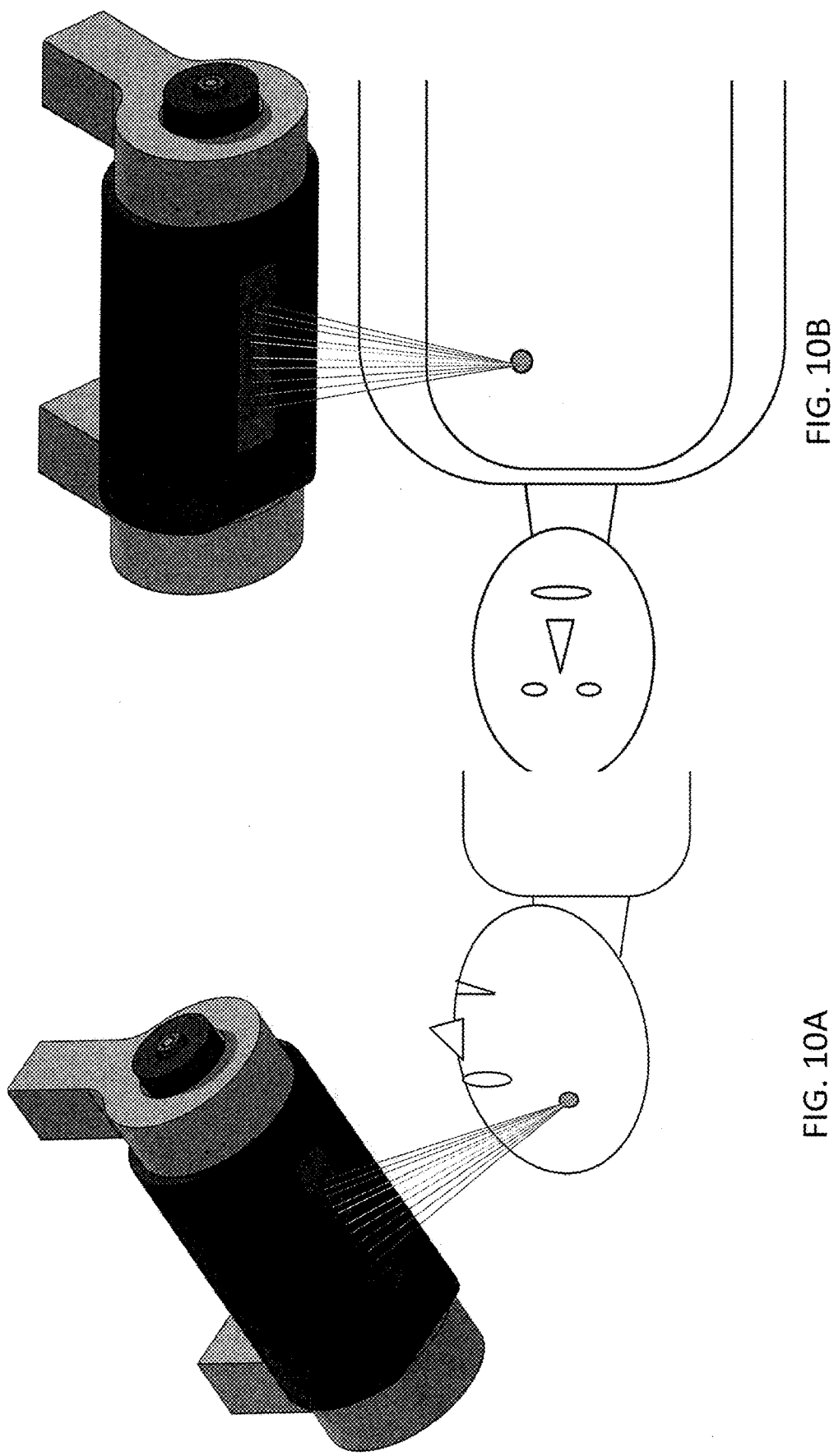
FIGS. 10A and 10B illustrate attachment of the radiation delivery device to a translation apparatus for movement of the delivery device to various bodily locations.

The compact design of radiation delivery devices described herein permit flexibility to treat diseased tissue at multiple locations in the body. The radiation delivery device can be attached to apparatus for translating the device to various body locations for radiation therapy. For example, the radiation delivery device can be easily moved from a head location to a thoracic location or extremity location in the arm and/or leg. FIGS. 10A and 10B illustrate attachment of the radiation delivery device to a translation apparatus for movement of the delivery device to various bodily locations.

In another aspect, methods of directing radiation are provided. In some embodiments, a method of directing radiation from a plurality of radiation sources comprises positioning a source body comprising the radiation sources within an interior cavity of a collimator component and directing the radiation to the common focal area with the collimator component. As described herein, the collimator component can comprise a primary collimator body including one or more sets of primary collimator passages for directing the radiation. The source body and/or primary collimator body can be rotated to align the radiation sources with the primary collimator passages. The collimator component may also comprise at least one additional collimator body having one or more sets of additional collimator passages for directing the radiation to the common focal point. In some embodiments, the additional collimator body is rotated to align a set of additional collimator passages with the primary collimator passages. Methods of delivering radiation described herein can be radiation therapy methods including, but not limited to, SRS and SBRT.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A radiation delivery device comprising:
a rotatable source component including a plurality of radiation sources;
a rotatable collimator component comprising a primary collimator body for directing radiation from the radiation sources to a common focal area; and
a shielding body, wherein the rotatable source component is positioned within an inner diameter of the primary collimator body, the rotatable source component rotatable independent of the primary collimator body.

2. The radiation delivery device of claim 1, wherein the primary collimator body comprises one or more sets of primary collimator passages for directing the radiation from the radiation sources.

3. The radiation delivery device of claim 2, wherein the rotatable collimator component further comprises at least one additional rotatable collimator body including one or more sets of additional collimator passages for directing the radiation from the radiation sources.

4. The radiation delivery device of claim 3, wherein the additional collimator passages are different than the primary collimator passages in shape and/or size.

5. The radiation delivery device of claim 3, wherein the primary collimator body is arranged within an interior cavity of the additional rotatable collimator body.

6. The radiation delivery device of claim 5, wherein sets of additional collimator passages are arranged at differing radial positions on the additional rotatable collimator body.

7. The radiation delivery device of claim 6, wherein the additional collimator passages arranged at differing radial positions have different shape and/or size.

8. The radiation delivery device of claim 5, wherein the rotatable source component exhibits a non-concentric arrangement with the primary collimator body and/or additional rotatable collimator body.

9. The radiation delivery device of claim 1, wherein the common focal area has a diameter or width of 2 mm to 60 mm.

10. The radiation delivery device of claim 1, wherein the radiation sources are arranged along a curved surface extending along the rotatable source component longitudinal axis.

11. The radiation delivery device of claim 1, wherein the radiation sources comprise radioactive material.

12. The radiation delivery device of claim 11, wherein the radioactive material is selected from the group consisting of cobalt-60, cesium-137 and iridium-192.

13. The radiation delivery device of claim 2, wherein the primary collimator body does not exhibit curvature in a region of the primary collimator passages.

14. The radiation delivery device of claim 3, wherein the one or more sets of additional collimator passages are unequal in number to the primary collimator passages.

15. A method of directing radiation from a plurality of radiation sources to a common focal area comprising:
 positioning a rotatable source component comprising the radiation sources within an inner diameter of a primary collimator body of a rotatable collimator component, the rotatable source component rotatable independent of the primary collimator body;
 rotating the rotatable source component from a position of the radiation sources facing a shielding body to a position of the radiation sources facing passages of the primary collimator body; and
 directing the radiation to the common focal area with the primary collimator body.

16. The method of claim 15, wherein the primary collimator body comprises one or more sets of primary collimator passages for directing the radiation.

17. The method of claim 16, wherein the rotatable collimator component further comprises at least one additional rotatable collimator body including one or more sets of additional collimator passages for directing the radiation to the common focal point.

18. The method of claim 17, wherein the additional collimator passages are different than the primary collimator passages in size and/or shape.

19. The method of claim 17, wherein the additional collimator passages differ in number from the primary collimator passages.

20. The method of claim 17, wherein the primary collimator body is arranged within an inner diameter of the additional rotatable collimator body.

21. The method of claim 20, wherein the rotatable source component, primary collimator body and/or additional rotatable collimator body are rotated to align the primary collimator passages and additional collimator passages with the radiation sources.

22. The method of claim 15, wherein the common focal area is located within a patient's body.

23. The method of claim 16, wherein the primary collimator body does not exhibit curvature in a region of the primary collimator passages.

24. The method of claim 17, wherein the one or more sets of additional collimator passages are unequal in number to the primary collimator passages.

25. The method of claim 24, wherein radiation dosage to the common focal area is varied by the unequal number of collimator passages in the one or more additional sets.

* * * * *